United States Patent [19]

Abraham et al.

[11] 4,161,608
[45] Jul. 17, 1979

[54] 11 HYDROXY METHYL 11-DEOXYPROSTAGLANDIN $E_1$

[75] Inventors: Nedumparambil A. Abraham, Dollard des Ormeaux; Jehan F. Bagli, Kirkland; Tibor Bogri, Montreal, all of Canada

[73] Assignee: Ayerst, McKenna and Harrison Limited, Montreal, Canada

[21] Appl. No.: 872,972

[22] Filed: Jan. 27, 1978

Related U.S. Application Data

[62] Division of Ser. No. 741,077, Nov. 11, 1976, Pat. No. 4,089,898, which is a division of Ser. No. 489,856, Jul. 19, 1974, Pat. No. 4,006,136, which is a division of Ser. No. 238,650, Mar. 27, 1972, Pat. No. 3,849,474.

[51] Int. Cl.$^2$ ............................................. C07C 177/00
[52] U.S. Cl. ................................... 560/121; 562/503; 260/410.9 R; 260/413
[58] Field of Search .................. 560/121; 562/503; 260/410.9 R, 413

[56] References Cited
U.S. PATENT DOCUMENTS
4,057,571  11/1977  Grudzinskas et al. ............... 560/121

Primary Examiner—Robert Gerstl
Attorney, Agent, or Firm—Arthur E. Wilfond

[57] ABSTRACT

A process for preparing 11-deoxyprostaglandin $E_1$, $E_2$ and $E_3$ and analogs thereof is realized by treating an appropriate di(lower)alkyl 3-(optionally substituted)-2-formylcyclopropane-1,1-dicarboxylate with an ylid prepared from a Wittig reagent of formula (AlkO)$_2$POCH$_2$CO—(c)-CH$_3$ in which Alk is an alkyl containing one to three carbon atoms and (c) is either (CH$_2$)$_q$ wherein q is an integer from 1 to 6 or cis CH$_2$CH=CH(CH$_2$)$_r$ wherein r is an integer from 0 to 3 to obtain the corresponding compound of formula:

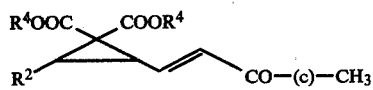

in which $R^2$ is hydrogen, lower alkyl or CH$_2$OR$^3$ wherein $R^3$ is lower alkanoyl, $R^4$ is lower alkyl and (c) is as defined herein. The latter compound is reduced with an alkali metal borohydride to yield the corresponding alcohol derivative. Condensation of this alcohol derivative or preferably its corresponding tetrahydropyran-2-yl ether derivative with a triester of formula CH(COOR$^6$)$_2$—(a)-(CH$_2$)pCOOR in which R and R$^6$ are lower alkyl, (a) is CH$_2$CH$_2$, cis CH=CH or C≡C and p is an integer from 2 to 4, gives the corresponding cyclopentanonetriester of formula

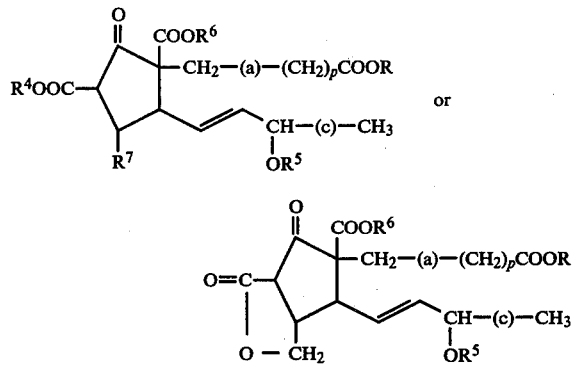

in which (a), (c), p, R, $R^4$ and $R^6$ are as defined herein, $R^5$ is hydrogen or tetrahydropyran-2-yl, respectively, and $R^7$ is hydrogen or lower alkyl; the lactonized form of the cyclopentanonetriester being obtained from said alcohol derivative in which $R^2$ is CH$_2$OR$^3$ wherein $R^3$ is lower alkanoyl. In the instance when $R^5$ is tetrahydropyran-2-yl the cyclopentanonetriester is treated with an acid to give the corresponding compound in which $R^5$ is hydrogen. The instant compound is then treated with a base under aqueous conditions, followed by optional esterification and acylation to give the desired 11-deoxy-prostaglandin derivatives of formula

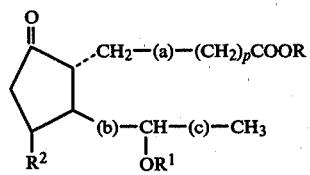

in which (a), (c) and p, are as defined herein, (b) is trans CH=CH, R is hydrogen or lower alkyl, $R^1$ is hydrogen or lower alkanoyl and $R^2$ is hydrogen, lower alkyl or CH$_2$OR$^3$ wherein $R^3$ is hydrogen or lower alkanoyl. The derivatives possess prostaglandin-like biological activity and methods for their use are given.

3 Claims, No Drawings

11 HYDROXY METHYL 11-DEOXYPROSTAGLANDIN E₁

This is a division of application Ser. No. 741,077, filed Nov. 11, 1976 now U.S. Pat. No. 4,089,898 which is a divisional of application Ser. No. 489,856 filed July 19, 1974, now U.S. Pat. No. 4,006,136 which is a divisional application of Ser. No. 238,650 filed Mar. 27, 1972, now U.S. Pat. No. 3,849,474.

BACKGROUND OF THE INVENTION

1. Field of Invention

This invention relates to prostaglandin derivatives. More particularly this invention relates to derivatives of 9,15-dioxygenated prostanoic acid and homologs thereof, to novel methods for producing these derivatives and to novel chemical intermediates useful in these methods.

2. Description of the Prior Art

Prostaglandins are naturally occurring C-20 fatty acids. The basic prostaglandin molecule contains a cyclopentane nucleus with two side chains. The chemistry and pharmacological effects of the prostaglandins have been the subject of several recent reviews; for example, see E. W. Horton, Physiol. Rev., 49, 122 (1969), J. F. Bagli in "Annual Reports in Medicinal Chemistry, 1969", C. K. Cain, Ed., Academic Press, New York and London, 1970, p. 170, and J. E. Pike in "Progress in the Chemistry of Organic Natural Products", Vol. 28, W. Herz, et al. Eds., Springer Verlag, New York, 1970, p. 313.

The pharmacological effects known to be associated with the prostaglandins relate to the reproductive, cardiovascular, respiratory, gastrointestinal and renal systems.

Due to the increasing interest in these natural products a rather extensive effort has been given recently to the synthesis of prostaglandins and their analogs. Included among these synthesis are several synthetic methods for the preparation of 9,15-dioxygenated derivatives of prostanoic or prost-13-enoic acids. For example, the synthesis of the first pharmacologically active 9,15-dioxygenated prostanoic acid derivative, 9ξ,15ξ-dihydroxyprost-13-enoic acid (11-desoxyprostaglandin F₁) was reported in detail by J. F. Bagli, T. Bogri and R. Deghenghi, Tetrahedron Letters, 465 (1966). A significant simplification and modification of that process was described by Bagli and Bogri in U.S. Pat. No. 3,455,992, issued July 15, 1969, whereby 9ξ,15ξ-dihydroxyprost-13-enoic acid as well as homologs thereof were obtained, see also Bagli and Bogri, Tetrahedron Letters, 5 (1967).

A further improvement in the synthesis of 9,15-dioxygenated derivatives of prostanoic acid has been described by Bagli and Bogri in Tetrahedron Letters, 1639 (1969), and German Offenlegungsschrift No. 1,953,232, published Apr. 30, 1970. This latter synthesis gave 9,15-dioxoprostanoic acid methyl ester and homologs thereof, from which a number of other 9,15-dioxygenated derivatives of prostanoic acid and of homologs thereof were prepared by conventional means.

A synthesis of 9,15-dioxygenated prostanoic and prost-13-enoic acid derivatives from 9,11,15-trioxygenated derivatives is reported in British patent specification No. 1,097,533, published Jan. 3, 1968. Among the derivatives prepared by this synthesis are the compounds of formula I of this invention in which (a) is $CH_2CH_2$, (b) is trans $CH=CH$, p is the integer 3, (c) is $(CH_2)_q$ wherein q is the integer 4, R is hydrogen or lower alkyl and $R^1$ and $R^2$ are hydrogen.

It is particularly noteworthy that the synthetic 9,15-dioxygenated prostanoic acid derivatives described above possess a number of the biological activities of the natural compounds although they lack the 11-hydroxyl of the latter.

Notwithstanding the fact that many of the syntheses reported to date are outstanding achievements, it is the purpose the present invention to provide an efficient, economical process that affords one or more of the following advantages over the earlier processes: (a) simplicity of operation, (b) versatility of its application to the preparation of 11-deoxy PGE₁, PGE₂ and PGE₃, analogs and 11-substituted derivatives thereof, (c) applicability to the preparation of higher and lower homologs thereof, and (d) the final products of this invention are readily reduced by known methods to the corresponding derivatives in the PGF series.

The present invention relates to an entirely new approach for the synthesis of 9,15-dioxygenated prostanoic acid derivatives which is unrelated to any of the above processes. The basis for this new approach is the unexpected discovery that an appropriately substituted dialkyl cyclopropane-1,1-dicarboxylate derivative condenses with an appropriately substituted dialkyl malonate derivative to give the corresponding cyclopentan-2-one-1,3-dicarboxylate derivative. The latter, upon appropriate transformations, thereafter is converted to the compounds of this invention, viz., cyclopentan-1-ones suitably substituted at positions 2 and 3 in a trans relationship with carbon side chains bearing the functional groups and the requisite degree of unsaturation analagous to the prostaglandin molecule, see the steps II+III→IV→I described hereinafter.

Although R. W. Kierstead et al., J. Chem. Soc., 3616 (1952) and R. Giuliano et al., Ann. Chim. (Rome), 50, 750 (1960), Chem. Abstr. 55, 3463 (1961) previously have condensed cyclopropane-1,1-dicarboxylate derivatives with dialkyl malonate or substituted derivatives thereof, the process of the present invention is readily distinguished from the prior art because decarboxylation of the intermediate tricarboxylate obtained by the process of this invention gives 2,3-disubstituted cyclopentan-1-one derivatives in which the side chains attached in trans-relationship to position 2 and 3 both carry functional groups, while the processes of the prior art were not capable of allowing the introduction of such side chains.

SUMMARY OF THE INVENTION

The prostaglandin derivatives of this invention may be represented by general formula I:

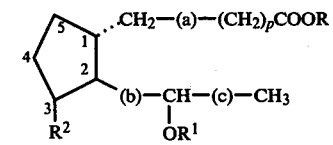

in which (a) is $CH_2CH_2$, cis $CH=CH$ or $C\equiv C$, p is an integer from 2 to 4, (b) is trans $CH=CH$, (c) is either $(CH_2)_q$ wherein q is an integer from 1 to 6 or cis $CH_2CH=CH(CH_2)_r$ wherein r is an integer from 0 to 3, R is hydrogen or lower alkyl, $R^1$ is hydrogen or lower alkanoyl and $R^2$ is hydrogen, lower alkyl or $CH_2OR^3$ wherein $R^3$ is hydrogen or lower alkanoyl, provided that $R^1$ is the same as $R^3$.

The prostaglandin derivatives of this invention may be prepared by a process involving a series of key steps which are represented schematically in the following manner:

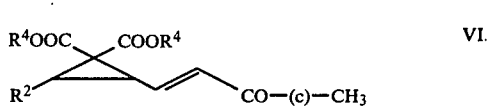

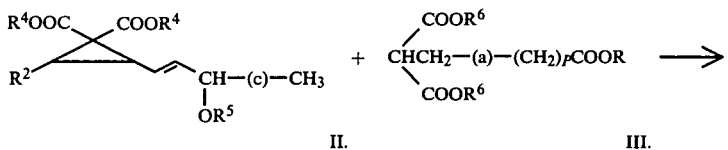

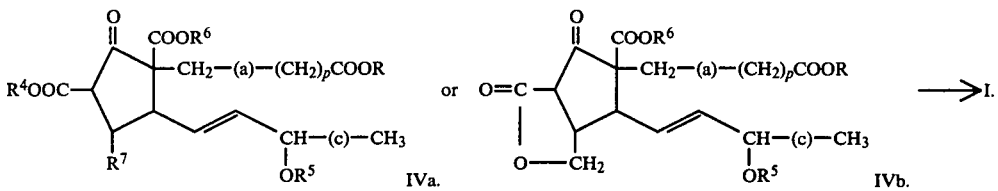

in which (a), (c) and p are as defined hereinbefore, R is lower alkyl, $R^2$ is hydrogen, lower alkyl or $CH_2OR^3$ in which $R^3$ is lower alkanoyl, $R^4$ is lower alkyl and $R^5$ is hydrogen or a radical suitable for protecting a hydroxyl, preferably tetrahydropyran-2-yl or tert-butyl, $R^6$ is lower alkyl and $R^7$ is hydrogen or lower alkyl.

In the preceding process the compound of formula II is subjected to a base catalyzed condensation with the triester of formula III to yield the cyclopentanonetriester of formulae IVa or IVb. The lactonized form of the cyclopentanonetriester, compound IVb, is obtained in this process when $R^2$ of compound II is $CH_2OR^3$ wherein $R^3$ is lower alkanoyl. In the instance when $R^5$ of the cyclopentanonetriester of formula IVa or IVb is a protecting radical, as defined hereinbefore, said cyclopentanonetriester is then treated with a suitable acid to remove the protecting radical whereby the corresponding cyclopentanonetriester of formulae IVa or IVb in which $R^5$ is H is obtained. The instant intermediate of formulae IVa or IVb is then treated with a base under aqueous conditions to give the corresponding compound of formula I in which R is hydrogen. Thereafter and if desired the latter compound is esterified to give the corresponding compound of formula I in which R is lower alkyl and if desired said latter compounds of formula I in which R is hydrogen or lower alkyl is acylated to give the corresponding compound of formula I in which $R^1$ and $R^3$ are lower alkanoyl.

According to a further feature of this invention a process for the preparation of compounds of formula II comprises the treatment of an aldehyde of formula V

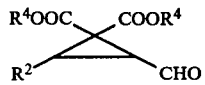

in which $R^2$ is hydrogen, lower alkyl or $CH_2OR^3$ in which $R^3$ is lower alkanoyl and $R^4$ is lower alkyl, with an ylid prepared from a Wittig reagent of formula (AlkO)$_2$POCH$_2$CO—(c)—CH$_3$ in which (c) is as defined in the first instance and Alk is an alkyl containing one to three carbons, in the presence of a suitable base to obtain a compound of formula VI in which $R^2$, $R^4$ and (c) are as defined above, reducing the latter compound with an alkali metal borohydride to obtain the compounds of formula II in which $R^5$ is hydrogen and if desired converting the latter compound to the corresponding compounds of formula II in which $R^5$ is a radical suitable for protecting a hydroxyl, preferably a tetrahydropyran-2-yl.

Still another feature of this invention is that the process described herein leads to the compounds of formula I in which the two side chains are in the trans configuration characteristic for the natural prostaglandins.

DETAILS OF THE INVENTION

The term "lower alkyl" as used herein contemplates straight or branched chain alkyl groups containing from one to three carbon atoms and straight alkyl chains containing from four to six carbon atoms and includes methyl, ethyl, propyl, isopropyl, butyl, pentyl and hexyl.

The term "lower alkanoyl" as used herein contemplates straight or branched chain alkanoyl radicals containing from two to five carbon atoms and includes acetyl, propiontyl, butyryl, isobutyryl, pentanoyl and pivaloyl.

The compound of formula I possess interesting pharmacological properties when tested in standard pharmacological tests. In particular, they have been found to possess hypotensive, antihypertensive, bronchospasmolytic, and gastric acid secretion inhibiting properties, which make them useful in the treatment of conditions associated with high blood pressure, in the treatment of asthmatic conditions and in the treatment of pathological conditions associated with excessive secretion of gastric acid such as, for example peptic ulcer. In addition, the compound of this invention inhibit the aggregation of platelets and promote the disaggregation of aggregated platelets, and are useful as agents for the prevention and treatment of thrombosis.

More particularly, these compounds, when tested in a modification of the tests for determining hypotensive activities described in "Screening Methods in Pharmacology", Academic Press, New York and London 1965, page 146, using the cat in urethane-chloralose anaesthesia as the test animal and measuring mean arterial blood pressure before and after intravenous administration of the compounds, have exhibited utility as hypotensive agents. When tested in the renal hypertensive rat prepared by the method of A. Grollman described in Proc. Soc. Exp. Biol. Med., 7, 102 (1954), and measuring blood pressure by the method described by H. Kersten, J. Lab. Clin. Med., 32, 1090 (1947), they have exhibited utility as antihypertensive agents.

Moreover, the compounds of this invention, when tested in a modification of the test method described by A. K. Armitage, et al., Brit. J. Pharmacol., 16, 59 (1961) have been found to alleviate bronchospasms, and are useful as bronchospasmolytic agents.

Furthermore, the compounds of this invention, when administered to rats in the test method described by H. Shay, et al., Gastroenterol, 26, 906 (1954), have been found to inhibit the secretion of gastric acid, and are useful as agents inhibiting the secretion of gastric acid.

In addition, the compounds of this invention, when tested in a modification of the test method described by G. V. R. Born, Nature, 194, 927 (1962), using the aggregometer manufactured by Bryston Manufacturing Limited, Rexdale, Ontario, Canada, have been shown to inhibit the aggregation of platelets and to promote the disaggregation of aggregated platelets, and are useful as agents for the prevention and treatment of thrombosis.

When the compounds of this invention are employed as hypotensive or anti-hypertensive agents, as agents inhibiting gastric acid secretion in warm-blooded animals, for example, in cats or rats, as agents for the prevention or treatment of thrombosis, or as bronchospasmolytic agents, alone or in combination with pharmacologically acceptable carriers, their proportions are determined by their solubilities, by the chosen route of administration, and by standard biological practice. The compounds of this invention may be administered orally in solid form containing such excipients as starch, lactose, sucrose, certain types of clay, and flavouring and coating agents. However, they are preferably administered parenterally in the form of sterile solutions thereof which may also contain other solutes, for example, sufficient sodium chloride or glucose to make the solution isotonic. For use as bronchospasmolytic agents, the compounds of this invention are preferably administered as aerosols.

The dosages of the present hypotensive, antihypertensive, gastric acid secretion inhibiting, or bronchospasmolytic agents, or agents for the prevention and treatment of thrombosis will vary with the forms of administration and the particular hosts under treatment. Generally, treatments are initiated with small dosages substantially less than the optimum doses of the compounds. Thereafter, the dosages are increased by small increments until the optimum effects under the circumstances are reached. In general, the compounds of this invention are most desirably administered at a concentration level that will generally afford effective results without causing any harmful or deleterious side effects and preferably at a level that is in a range of from about 0.1 mg. to about 10.0 mg. per kilo, although as aforementioned variations will occur. However, a dosage level that is in range of from about 0.5 mg. to about 5 mg. per kilo is most desirably employed in order to achieve effective results. When administering the compounds of this invention as aerosols the liquid to be nebulized, for example, water, ethyl alcohol, dichlorotetrafluoroethane and dichlorodifluoromethane, contains preferably from 0.005–0.05 percent of the acid, or a non-toxic alkali metal, ammonium or amine salt thereof, or ester of formula I.

Furthermore, when the compounds of this invention are tested by the method of A. P. Labhsetwar, Nature, 230, 588 (1971) whereby the compound is given subcutaneously on a daily basis to mated hamsters on days 4,5 and 6 of pregnancy, thereafter the animals being sacrificed on day 7 of pregnancy and the number of abortions counted, the compounds are shown to have abortifacient properties. Also the compounds of this invention are useful for inducing labor in pregnant animals at or near term. When the compounds of this invention are employed as agents for abortion or for inducing labor, the compound may be infused intravenously at a dose 0.01 to 500 mg./kg. per minute until the desired effect is obtained.

PROCESS

As noted hereinbefore the preparation of the compounds of this invention involve the base catalyzed condensation of a compound of formula II in which (c), $R^4$ and $R^5$ are as defined in the first instance and $R^2$ is hydrogen, lower alkyl, or $CH_2OR^3$ in which $R^3$ is lower alkanoyl with a triester of formula III in which (a) and p are as defined in the first instance and R is lower alkyl.

The compound of formula II for this key reaction prepared as follows:

A di(lower)alkylbromomalonate, for example, dimethylbromomalonate, prepared by using the procedure for diethyl bromomalonate, "Organic Syntheses", Collect Vol. 1, 2nd ed., A. H. Blatt, Ed, John Wiley & Sons, New York, N.Y., 1956, p. 245, is condensed in the presence of an alkali metal lower alkoxide in a lower alkanol, preferably sodium methoxide in methanol, with acrolein; an $\alpha,\beta$-unsaturated aldehyde of formula (lower alkyl)—CH=CH—CHO (see "Rodd's Chemistry of the Carbon Compounds", S. Coffey, Ed., Vol. 1c, 2nd Ed. pp. 48–51), for example, crotonaldehyde, 2-hexenal, and the like; or a γ-(lower alkanoyloxy)-crotonaldehyde, preferably γ-acetoxycrotonaldehyde (prepared by treating γ-acetoxycrotonaldehyde diacetate, H. Schmid and E. Grob, Helv. Chim. Acta, 32, 77 (1949), with one equivalent of water in a lower alkanol); to yield a cyclopropanealdehyde derivative of formula V, i.e. a di(lower)alkyl 2-formylcyclopropane-1,1-dicarboxylate, the corresponding 3-lower alkyl analog or the corresponding 3-(lower alkanoyloxymethyl) analog, respectively. The reaction conditions described by D. T. Warner, J. Organic Chemistry, 24, 1536 (1959) for the preparation of the cyclopropanealdehyde derivatives, diethyl 2-formyl cyclopropane-1,1-dicarboxylate and its corresponding 3-methyl analog, are convenient and quite satisfactory for this condensation.

The cyclopropanealdehyde derivative of formula V so obtained is then treated with the ylid prepared from Wittig reagent, of the formula $(AlkO)_2P(O)CH_2CO$—(c)—$CH_3$ in which (c) is as defined hereinbefore, and Alk is an alkyl containing from 1 to 3 carbon atoms, preferably a dimethyl 2-oxoalkylphosphonate, in the presence of an alkali metal hydride, preferably sodium hydride, and in an aprotic solvent, preferably dimethoxyethane. Acidification with an aqueous acid, preferably aqueous acetic acid, extraction with a water—immiscible solvent, preferably diethyl ether, followed by washing, drying and evaporation of the latter, yields the corresponding compound of formula VI in which $R^2$ is hydrogen, lower alkyl or $CH_2OR^3$ in which $R^3$ is lower alkanoyloxy.

The requisite Wittig reagents are either known, for example, dimethyl 2-oxoheptylphosphonate, E. J. Corey, et al., J. Am. Chem. Soc., 90, 3247 (1968) or they may be prepared by the method of E. J. Corey and G. T. Kwiatkowski, J. Am. Chem. Soc., 88, 5654 (1966) using the appropriate lower alkyl alkanoate or lower alkyl alkenoate and di(lower)alkyl α-lithiomethanephosphonate.

More specifically, the treatment of the cyclopropanealdehyde derivative of formula V with the ylid is performed in the following manner. A solution of the Wittig reagent in about 5 to 10 parts of an aprotic solvent, preferably dimethoxyethane, is added slowly under a blanket of nitrogen to a stirred suspension of approximately one equivalent of an alkali metal hydride, preferably sodium hydride, in approximately 150 parts of the aprotic solvent and stirring is continued at room temperature for a period of time of from 10 to 60 minutes, preferably for about 30 minutes. To the resulting solution of the corresponding ylid there is slowly added a solution of approximately three quarters to one equivalent, preferably about 0.85 equivalent, of the appropriate cyclopropanealdehyde derivative described above in about 5–10 parts, preferably about 8 parts of an aprotic solvent, preferably dimethoxyethane. The addition is carried out at room temperature over a period of time of from 5 to 30 minutes, preferably about 10 minutes, and stirring is continued for another 10 to 60 minutes, preferably for about 30 minutes. Acidification with an aqueous acid, preferably aqueous acetic acid, followed by extraction with a water—immiscible solvent, preferably diethyl ether, washing and drying of the extracts, evaporation of the solvent, and chromatography of the residue on silica gel yields the corresponding compound of formula VI in which (c) is as defined hereinbefore, $R^2$ is hydrogen, lower alkyl or $CH_2OR^3$ wherein $R^3$ is lower alkanoyloxy and $R^4$ is lower alkyl.

As an alternative to the above preferred procedure, the compounds of formula VI in which $R^2$ is hydrogen and (c) is $(CH_2)_q$ wherein q is an integer from 1 to 6 are prepared in the following manner: A chlorovinyl ketone of formula $ClCH=CHCO(CH_2)_nCH_3$ in which n is an integer from 1 to 6, prepared by the general procedure described for the preparation of 1-chloro-6-methyl-1-hepten-3-one in Organic Syntheses, 32, 27 (1952), is converted to its corresponding di(lower)alkylaminovinyl ketone by treatment with an excess, for example two to five molar equivalents, of a di(lower)alkylamine, preferably 40% aqueous dimethylamine at room temperature for 20 minutes. The aminovinyl ketone is then reacted with a vinyl magnesium halide, preferably vinyl magnesium bromide, in an inert solvent, preferably dry tetrahydrofuran or ether. Preferred conditions for this reaction include a temperature range from room temperature to the boiling point of the mixture and a reaction time of 30 minutes to four hours. In this manner the dienone of formula $CH_2=CHCH=CHCO(CH_2)_nCH_3$ in which n is an integer from 1 to 6 is obtained.

The same dienone is obtained also by treating the aminovinyl ketone, described above with lithium acetylide or an acetylene Grignard reagent, for example, ethynyl magnesium bromide or preferably lithium acetylide-ethylenediamine complex, in an inert solvent, preferably dioxane, under essentially the same conditions described above for the reaction of a vinyl magnesium halide whereby said aminovinyl ketone yields a compound of formula (lower alkyl)$_2$NCH(C≡CH)CH$_2$CO(CH$_2$)$_n$CH$_3$ in which n is an integer from 1 to 6. Treatment of the latter compound with an excess of acid, for example, 1.2 to 2.5 molar equivalents of hydrochloric, sulfuric or preferably p-toluenesulfonic acid, in an inert solvent, for example, methanol or tetrahydrofuran, to effect the elimination of one molecule of di(lower)alkyl amine, followed by hydrogenation of the corresponding alkenynone product of formula $-HC\equiv CCH=CHCO(CH_2)_nCH_3-$ in which n is as described above, obtained therefrom, in the presence of Lindlar catalyst affords the dienone of formula $CH_2=CHCH=CHCO(CH_2)_nCH_3$ described above.

The latter dienone is now treated with a di(lower)alkyl bromomalonate, described above, in the presence of an alkali metal lower alkoxide to yield the desired compound of formula VI in which $R^2$ is hydrogen, $R^4$ is lower alkyl and (c) is $(CH_2)_q$ wherein q is an integer from 1 to 6. More specifically this reaction is effected by adding simultaneously a solution of the dienone in a lower alkanol, for example, ethanol, and a solution of about one equivalent of an alkali metal lower alkoxide, for example, sodium ethoxide, in the same lower alkanol as above, to an agitated solution of approximately one equivalent of the di(lower)alkyl bromomalonate, for example, diethyl bromomalonate, in the same lower alkanol described above. The temperature during addition may range from −20° to 60° C., preferably 0° to 20° C. After completion of the addition, the mixture is stirred for about three hours at the same temperature then at room temperature for a further eight to 24 hours. Thereafter the mixture is neutralized with acid, preferably acetic acid, the precipitated alkali metal bromide separated by filtration, and the reaction mixture concentrated. The residue is purified on silica gel to yield the desired compound of formula VI.

Thereafter, the compound of formula VI in which (c) is as defined in the first instance, $R^2$ is hydrogen, lower alkyl or $CH_2OR^3$ wherein $R^3$ is lower alkanoyloxy and $R^4$ is lower alkyl is reduced with an alkali metal borohydride, potassium borohydride or preferably sodium borohydride, in an inert solvent to yield a mixture of epimers of the desired compound of formula II in which $R^5$ is hydrogen. The epimers result from the assymetric center at the carbon to which the secondary alcohol is attached. The mixture of epimers need not be separated at this stage. In practice it has been found more convenient to continue the process with the mixture of epimers and if desired separate the resulting epimers of compounds of formula I.

Thereafter and if desired, the compound of formula II in which $R^5$ is hydrogen is converted to the corresponding compound of formula II in which $R^5$ is a radical suitable for protecting a hydroxyl, preferably a tetrahydropyran-2-yl which is readily formed by treating said latter compound with dihydropyran in the presence of an acid catalyst; for instance, p-toluenesulfonic acid is preferred. Sulfuric acid is also a suitable catalyst for this purpose.

The triester of formula III for the above key reaction is prepared in the following manner:

The triester of formula III in which (a) is C≡C, noted above, is prepared by a process which is represented schematically in the following manner:

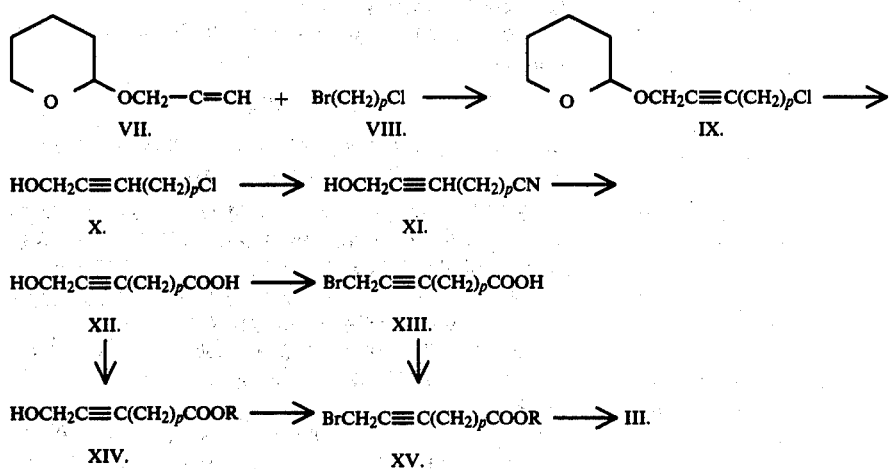

HOCH₂C≡CH(CH₂)ₚCl ⟶ HOCH₂C≡CH(CH₂)ₚCN ⟶

X.                            XI.

HOCH₂C≡C(CH₂)ₚCOOH ⟶ BrCH₂C≡C(CH₂)ₚCOOH

XII.                       XIII.

↓                             ↓

HOCH₂C≡C(CH₂)ₚCOOR ⟶ BrCH₂C≡C(CH₂)ₚCOOR ⟶ III.

XIV.                      XV.

in which p is as defined in the first instance and R is lower alkyl.

With reference to the preceding process propargyl alcohol tetrahydropyran-2-yl ether, described by R. G. Jones and M. J. Mann, J. Amer. Chem. Soc., 75, 4048 (1953), is condensed with a dihaloalkane of formula VIII to give the tetrahydropyranyl ether of formula IX according to the procedure of A. I. Rachlin, et al., J. Org. Chem., 26, 2688 (1961), used to prepare 1-[(tetrahydropyran-2-yl)oxy]-6-chloro-2-hexyne. The tetrahydropyranyl ether of formula IX is hydrolyzed, for example, with p-toluenesulfonic acid in aqueous methanol, to its corresponding alcohol of formula X, see also the procedure of Rachlin, cited above, for the preparation of 6-chloro-2-hexyn-1-ol (X, p=3). The alcohol X is then treated with potassium or sodium cyanide in a lower alkanol, preferably with potassium cyanide in ethanol, at reflux temperature for eight to 24 hours to give the cyanide XI. Subsequently a solution containing an excess of potassium hydroxide in water is added to the reaction mixture of the cyanide XI and the resultant mixture is heated at reflux for a further ten to 20 hours whereby the cyanide XI is converted to the corresponding hydroxyacid XII. The latter compound is then brominated by treatment with phosphorus tribromide in ether solution in the presence of a suitable proton acceptor, for example, pyridine, to yield the corresponding bromoacid XIII, which is esterified with a lower alkanol, for example, methanol in the presence of a suitable acid catalyst, for example, p-toluenesulfonic acid, to give the corresponding bromoester of formula XV.

Alternatively, the order of the latter two steps of bromination and esterification are reversed whereby the hydroxyacid XII is converted to the bromoester of formula XV via the hydroxy ester XIV.

Optionally, the corresponding chloroester of the bromoester of formula XV is prepared by the preceding process by replacing the dihaloalkane of formula VIII with its corresponding α-iodo-(ω)-chloroalkane. The chloroester so obtained is used in the same manner as described herein for said bromoester.

Thereafter the desired triester of formula III in which (a) is C≡C is obtained by condensing the above bromoester of formula XV with a dialkylmalonate, in the presence of an alkali metal alkoxide in a lower alkanol. More particularly, the condensation is performed by adding the dialkylmalonate portionwise to a solution of on equivalent of sodium methoxide in methanol at a temperature of from 10° to 30° C., preferably room temperature. After stirring for about 10 to 20 minutes, the reaction mixture is treated portionwise with one equivalent of the bromoester of formula XV followed by heating the reaction mixture at reflux temperature for one to two hours. Thereafter, dilution of the mixture with water, extraction with a water-immiscible solvent, preferably ether, washing and drying of the extract, followed by removal of the solvent gives a residue, which on purification by distillation under reduced pressure gives the desired triester III in which (a) is C≡C.

The triesters of formula III in which (a) is cis CH=CH or CH₂CH₂ are prepared by condensing the appropriate lower alkyl ω-haloalkanoate with a dialkylmalonate in the same manner as just described for the preparation of triester III in which (a) is C≡C. The appropriate lower alkyl ω-haloalkanates, for this condensation are either known or are prepared by known methods; for example, by hydrogenation of the bromoesters of formula XV or its corresponding chloroester, see also "Rodd's Chemistry of the Carbon Compounds", cited above, Vol. 1c, pp. 201–252.

Alternatively, the triester of formula III in which (a) is cis CH=CH is prepared by hydrogenation of the corresponding triester of formula III in which (a) is C≡C, described above, in the presence of Lindlar catalyst.

The compound of formula II and the triester of formula III, prepared as described above, are now subjected to a base catalyzed condensation to give the cyclopentanonetriester of formula IVa and IVb. More specifically, the condensation is performed in the presence of suitable base, preferably an alkali metal alkoxide, for example, sodium methoxide. Other suitable bases include sodium ethoxide, potassium tert-butoxide, and sodium hydride. In particular, this condensation may be conveniently effected by heating a mixture of about equimolar amounts of the compound of formula II and the triester III at 100° to 150° C., preferably 135°–140° C., for 30 minutes to three hours, preferably one hour. The reaction mixture is then cooled, treated with saturated sodium chloride solution neutralized with an acid, for example, acetic acid, and extracted with a water-immiscible solvent, for example, ether. Evaporation of the extract and purification of the residue by chromatography on silica gel yields the cyclopentanonetriester of formulae IVa or IVb.

Although compounds of formula II in which $R^5$ is either hydrogen or a protecting radical as defined above undergo the above base catalyzed condensation, it is preferable to use those compounds of formula II having the protecting group. In the latter case following the condensation the protecting group is then removed. More explicitly in a preferred embodiment the base catalyzed condensation is effected with a compound in which $R^5$ is tetrahydropyran-2-yl and thereafter the tetrahydropyran-2-yl protecting group is removed by treating the resulting cyclopentanonetriester of formula IV ($R^5$=tetrahydropyran-2-yl) with acid, for example, hydrochloric acid, aqueous acetic acid or preferably p-toluenesulfonic acid, in an inert solvent in the presence of water, preferably methanol-water (9:1).

The cyclopentanonetriester (IVa or IVb) is now treated with an alkali metal hydroxide under aqueous conditions to give the compounds of formula I in which (a), (b), (c) and p are as defined in the first instance, R and $R^1$ are hydrogen and $R^2$ is hydrogen, lower alkyl or $CH_2OR^3$ wherein $R^3$ is hydrogen. Preferably this reaction is done by heating a mixture of the cyclopentanonetriester with an alkali metal hydroxide, preferably sodium hydroxide or potassium hydroxide, under aqueous conditions at reflux temperature of the mixture for a period of 15 minutes to three hours, preferably about one hour. Neutralization of the reaction mixture with acid, for example, 2 N HCl, extraction with a water-immiscible solvent, for example, ether, and subsequent work up of the extract yields a mixture of epimers of compounds of formula I in which R and $R^1$ are hydrogen and $R^2$ is hydrogen, lower alkyl or $CH_2OR^3$ wherein $R^3$ is hydrogen. If desired the epimers may be conveniently separated at this stage by chromatography on silica gel. For convenience the less polar epimer is designated epimer A and the more polar, epimer B.

Thereafter and if desired the latter compounds are esterified with a lower alkanol, for example, methanol, ethanol or propanol, in the presence of a acid, for example, sulfuric acid, hydrochloric acid or preferably perchloric acid, to give the corresponding ester compounds of formula I in which (a), (b), (c) and p are as defined in the first instance, R is lower alkyl, $R^1$ is hydrogen and $R^2$ is hydrogen, lower alkyl or $CH_2OR^3$ wherein $R^3$ is hydrogen.

Within this latter group of compounds of formula I is the compound, 9-oxo-15-hydroxyprost-13-enoic acid methyl ester (I; (a)=$CH_2CH_2$, (b)=trans CH=CH, p=3, (c) is $(CH_2)_q$ wherein q is the integer 4, and R is methyl, $R^1$ and $R^2$=H). By means of spectroscopic evidence this particular prostaglandin derivative has been shown to be identical with the same compound described in British patent specification No. 1,097,533, noted above.

Finally, if desired the above compounds of formula I in which R is hydrogen or lower alkyl are acylated by treatment with an appropriate lower alkanoic anhydride or lower alkanoic acid chloride in the presence of pyridine to give the corresponding compounds of formula I in which (a), (b), (c) and p are as defined in the first instance, R is hydrogen or lower alkyl, $R^1$ is lower alkanoyl and $R^2$ is hydrogen, lower alkyl or $CH_2OR^3$ wherein $R^3$ is lower alkanoyl.

The following examples illustrate further this invention.

EXAMPLE 1

Dimethyl 2-Formylcyclopropane-1,1-dicarboxylate (V, $R^2$=H and $R^4$=$CH_3$)

By following the procedure of D. T. Warner, cited above, used for preparing diethyl 2-formylcyclopropane-1,1-dicarboxylate from acrolein but using equivalent amount of dimethylbromomalonate and methanol instead of diethylbromomalonate and ethanol, respectively, the title compound, nmr (CDCl$_3$) δ 1.98 (m,2H), 2.80 (m,1H), 3.79 (s,6H), 8.82 (d, J=4 cps, 1H), is obtained.

In the same manner but replacing acrolein with an equivalent amount of crotonaldehyde, 2-pentenal, 2-hexenal or γ-acetoxycrotonaldehyde, the following compounds of formula V, dimethyl 2-formyl-3-methylcyclopropane-1,1-dicarboxylate, dimethyl 2-formyl-3-ethylcyclopropane-1,1-dicarboxylate dimethyl 2-formyl-3-propylcyclopropane-1,1-dicarboxylate, dimethyl 3-(acetoxymethyl)-2-formylcyclopropane-1,1-dicarboxylate are obtained, respectively.

Likewise the corresponding diethyl and dipropyl esters of the above compounds of formula V are obtained by the choice of appropriate starting materials. For example, by using diethylbromomalonate, ethanol and γ-acetoxycrotonaldehyde, diethyl 3-(acetoxymethyl)-2-formylcyclopropane-1,1-dicarboxylate, $\gamma_{max}^{film}$ 2730, 1730 cm$^{-1}$, is obtained.

γ-Acetoxycrotonaldehyde is prepared by treating γ-acetoxycrotonaldehyde diacetate, H. Schmid and E. Grob, Helv. Chem. Acta, 32, 77 (1949), with one equivalent of water in a lower alkanol, for example, ethanol.

EXAMPLE 2

Dimethyl trans-2-(3-Oxo-1-octenyl)cyclopropane-1,1-dicarboxylate [VI, $R^2$=H, $R^4$=$CH_3$ and (c)=$(CH_2)_4$]

To 5.56 g of a 50% sodium hydride (NaH) suspension, rinsed with dry hexane, suspended in 400 ml dry 1,2-dimethoxyethane is added 27.4 g of the Wittig reagent, dimethyl(2-oxoheptyl)phosphonate, in 400 ml dry 1,2-dimethoxyethane. The reaction mixture is stirred at room temperature till all NaH reacts to give the sodium salt (about 45 minutes). A solution of 21.6 g of dimethyl 2-formylcyclopropane-1,1-dicarboxylate (V, $R^2$=H and $R^4$=$CH_3$), described in Example 1, in 350 ml dry 1,2-dimethoxyethane is added and the mixture is heated at 60° C. for ½ hr; cooled, and acetic acid is added to render the mixture substantially neutral. After diluting with water the mixture is extracted with ether. The extract is washed with water, dried (MgSO$_4$) and evaporated. The residue is purified by chromatography on silica gel to yield the title compound, nmr (CDCl$_3$) δ 0.88 (t,3H), 1.77 (m,2H), 3.77 (s,3H).

By following the procedure of Example 2 and utilizing the appropriate Wittig reagent and compound of formula V then other compounds of formula VI are prepared. Examples of such compounds of formula V are listed in Table I together with the appropriate Wittig reagent and compound of formula V utilized for their preparation.

TABLE I

| | WITTIG REAGENT (AlkO)$_2$P(O)CH$_2$CO-(c)-CH$_3$) | | COMPOUND OF FORMULA V | | PRODUCT: (PREFIX LISTED BELOW) |
|---|---|---|---|---|---|
| Ex. | Alk | (c) | R$^2$ | R$^4$ | CYCLOPROPANE-1,1-DICARBOXYLATE |
| 3 | CH$_3$ | CH$_2$ | H | CH$_3$ | dimethyl trans-2-(3-oxo-1-pentenyl) |
| 4 | CH$_3$ | (CH$_2$)$_4$ | H | C$_2$H$_5$ | diethyl trans-2-(3-oxo-1-octenyl) |
| 5 | CH$_3$ | (CH$_2$)$_3$ | H | CH$_3$ | dimethyl trans-2-(3-oxo-1-heptenyl) |
| 6 | CH$_3$ | (CH$_2$)$_5$ | H | CH$_3$ | dimethyl trans-2-(3-oxo-1-nonenyl) |
| 7 | CH$_3$ | (CH$_2$)$_6$ | H | CH$_3$ | dimethyl trans-2-(3-oxo-1-decenyl) |
| 8 | CH$_3$ | CH$_2$CH=CH | H | CH$_3$ | dimethyl trans-2-(3-oxo-1,5-heptadienyl) |
| 9 | CH$_3$ | CH$_2$CH=CHCH$_2$ | H | CH$_3$ | dimethyl trans-2-(3-oxo-1,5-octadienyl) |
| 10 | CH$_3$ | CH$_2$CH=CH(CH$_2$)$_2$ | H | CH$_3$ | dimethyl trans-2-(3-oxo-1,5-nonadienyl) |
| 11 | CH$_3$ | CH$_2$CH=CH(CH$_2$)$_3$ | H | CH$_3$ | dimethyl trans-2-(3-oxo-1,5-decadienyl) |
| 12 | CH$_3$ | CH$_2$ | CH$_3$ | CH$_3$ | dimethyl trans-3-methyl-2-(3-oxo-1-pentenyl) |
| 13 | CH$_3$ | (CH$_2$)$_2$ | CH$_3$ | CH$_3$ | dimethyl trans-3-methyl-2-(3-oxo-1-hexenyl) |
| 14 | CH$_3$ | (CH$_2$)$_3$ | CH$_3$ | CH$_3$ | dimethyl trans-3-methyl-2-(3-oxo-1-heptenyl) |
| 15 | CH$_3$ | (CH$_2$)$_4$ | CH$_3$ | CH$_3$ | dimethyl trans-3-methyl-2-(3-oxo-1-octenyl) |
| 16 | CH$_3$ | (CH$_2$)$_5$ | CH$_3$ | CH$_3$ | dimethyl trans-3-methyl-2-(3-oxo-1-nonenyl) |
| 17 | CH$_3$ | (CH$_2$)$_6$ | CH$_3$ | CH$_3$ | dimethyl trans-3-methyl-2-(3-oxo-1-decenyl) |
| 18 | CH$_3$ | CH$_2$CH=CH | CH$_3$ | CH$_3$ | dimethyl trans-3-methyl-2-(3-oxo-1,5-heptadienyl) |
| 19 | CH$_3$ | CH$_2$CH=CHCH$_2$ | CH$_3$ | CH$_3$ | dimethyl trans-3-methyl-2-(3-oxo-1,5-octadienyl) |
| 20 | CH$_3$ | CH$_2$CH=CH(CH$_2$)$_2$ | CH$_3$ | CH$_3$ | dimethyl trans-3-methyl-2-(3-oxo-1,5-nonadienyl) |
| 21 | CH$_3$ | CH$_2$CH=CH(CH$_2$)$_3$ | CH$_3$ | CH$_3$ | dimrthyl trans-3-methyl-2-(3-oxo-1,5-decadienyl) |
| 22 | CH$_3$ | CH$_2$ | C$_2$H$_5$ | CH$_3$ | dimethyl trans-3-ethyl-2-(3-oxo-1-pentenyl) |
| 23 | CH$_3$ | (CH$_2$)$_4$ | C$_2$H$_5$ | CH$_2$H$_5$ | diethyl trans-3-ethyl-2-(3-oxo-1-octenyl) |
| 24 | CH$_3$ | (CH$_2$)$_6$ | C$_2$H$_5$ | CH$_3$ | dimethyl trans-3-ethyl-2-(3-oxo-1-decenyl) |
| 25 | C$_2$H$_5$ | CH$_2$CH=CH | C$_2$H$_5$ | C$_2$H$_5$ | diethyl trans-3-ethyl-2-(3-oxo-1,5-heptadienyl) |
| 26 | C$_2$H$_5$ | CH$_2$CH=CHCH$_2$ | C$_2$H$_5$ | C$_2$H$_5$ | diethyl trans-3-ethyl-2-(3-oxo-1,5-octadienyl) |
| 27 | CH$_3$ | (CH$_2$)$_2$ | n-C$_3$H$_7$ | CH$_3$ | dimethyl trans-3-propyl-2-(3-oxo-1-hexenyl) |
| 28 | CH$_3$ | (CH$_2$)$_4$ | n-C$_3$H$_7$ | CH$_3$ | dimethyl trans-3-propyl-2-(3-oxo-1-octenyl) |
| 29 | CH$_3$ | (CH$_2$)$_5$ | i-C$_3$H$_7$ | C$_2$H$_5$ | diethyl trans-3-isopropyl-2-(3-oxo-1-nonenyl) |
| 30 | C$_2$H$_5$ | CH$_2$CH=CH(CH$_2$)$_2$ | i-C$_3$H$_7$ | CH$_3$ | dimethyl trans-3-isopropyl-2-(3-oxo-1,5-nondienyl) |
| 31 | C$_2$H$_6$ | CH$_2$CH=CH(CH$_2$)$_3$ | n-C$_3$H$_7$ | CH$_3$ | dimethyl trans-3-propyl-2-(3-oxo-1,5-decadienyl) |
| 32 | CH$_3$ | (CH$_2$)$_3$ | AcOCH$_2$ | CH$_3$ | dimethyl trans-3-(acetoxymethyl)-2-(3-oxo-1-heptenyl) |
| 33 | CH$_3$ | (CH$_2$)$_4$ | AcOCH$_2$ | C$_2$H$_5$ | diethyl trans-3-(acetoxymethyl)-2-(3-oxo-1-octenyl), $\gamma_{max}^{film}$ 1730,1690, 1670,1625 cm$^{-1}$ |
| 34 | CH$_3$ | (CH$_2$)$_6$ | AcOCH$_2$ | C$_2$H$_5$ | diethyl trans-3-(acetoxymethyl)-2-(3-oxo-1-decenyl) |
| 35 | CH$_3$ | CH$_2$CH=CH | AcOCH$_2$ | C$_2$H$_5$ | diethyl trans-3-(acetoxymethyl)-2-(3-oxo-1,5-heptadienyl) |
| 36 | CH$_3$ | CH$_2$CH=CHCH$_2$ | AcOCH$_2$ | C$_2$H$_5$ | diethyl trans-3-(acetoxymethyl)-2-(3-oxo-1,5-octadienyl) |

EXAMPLE 37

1-(Dimethylamino)-1-octen-3-one

A solution of dimethylamine (560 ml, 40% aqueous) is cooled to 5° C. 1-Chloro-1-octen-3-one (192 g) is added and the mixture stirred at room temperature for 20 min. The solution is then saturated with potassium carbonate and extracted with ether. The organic layer is washed 3× with sat. sodium chloride solution, dried over sodium sulfate, concentrated and distilled to give the title compound, b.p. 94°-96° C./0.2 mm.

In the same manner but replacing 1-chloro-1-octen-3-one with an equivalent amount of 1-chloro-1-penten-3-one, 1-chloro-1-hexen-3-one, 1-chloro-1-hepten-3-one, 1-chloro-1-nonen-3-one or 1-chloro-1-decen-3-one, then 1-(dimethylamino)-1-penten-3-one, 1-(dimethylamino)-1-hexen-3-one, 1-(dimethylamino)-1-hepten-3-one, 1-(dimethylamino)-1-nonen-3-one and 1-(dimethylamino)-1-decen-3-one are obtained, respectively.

EXAMPLE 38

1,3-Decadien-5-one

To a solution of Grignard reagent prepared from vinyl bromide (10.7 g), and magnesium (2.43 g) in dry tetrahydrofuran (40 ml) is added gradually a solution of 1-(dimethylamino)-1-octen-3-one (16.9 g), described in Example 37, in dry tetrahydrofuran (20 ml). The mixture is stirred and heated to reflux for 1 hr. The reaction mixture is cooled to room temperature, diluted with ether, washed with hydrochloric acid (10 ml), followed by saturated ammonium chloride solution. The ether extract is dried, and the solvent is removed. The residue is chromatographed to yield the title compound, $\lambda_{max.}^{EtOH}$ 260 nm ($\epsilon = 17,050$), $\gamma_{max}^{film}$ 1686, 1668 cm$^{-1}$.

In the same manner but replacing 1-(dimethylamino)-1-octen-3-one with an equivalent amount of 1-(dimethylamino)-1-penten-3-one, 1-(dimethylamino)-1-hexen-3-one, 1-(dimethylamino)-1-hepten-3-one, 1-(dimethylamino)-1-nonen-3-one or 1-(dimethylamino)-1-decen-3-one, then 1,3-heptadien-5-one, 1,3-octadien-5-one, 1,3-nonadien-5-one, 1,3-undecadien-5-one and 1,3-dodecadien-5-one are obtained, respectively.

EXAMPLE 39

3-(Dimethylamino)-1-decyn-5-one

A mixture of 1-(dimethylamino)-1-octen-3-one (4.0 g), described in Example 37, and lithiumacetylide-ethyleneamine (4.0 g) in dry dioxane (25 ml) is stirred at room temperature for 45 min. The mixture is added to ice. The mixture is extracted with ether. The extract is dried (Na$_2$SO$_4$) and then evaporated. The residue is distilled to afford the title compound, b.p. 80°–85° C.

In the same manner but replacing 1-(dimethylamino)-1-octen-3-one with an equivalent amount of 1-(dimethylamino)-1-penten-3-one, 1-(dimethylamino)-1-hexen-3-one, 1-(dimethylamino)-1-hepten-3-one, 1-(dimethylamino)-1-nonen-3-one or 1-(dimethylamino)-1-decen-3-one, described in Example 37, then 3-(dimethylamino)-1-heptyn-5-one, 3-(dimethylamino)-1-octyn-5-one, 3-(dimethylamino)-1-nonyn-5-one, 3-(dimethylamino)-1-undecyn-5-one and 3-(dimethylamino)-1-dodecyn-5-one are obtained, respectively.

EXAMPLE 40

1,3-Decadien-5-one

To a solution of 3-(dimethylamino)-1-decyn-5-one (2.2 g), described in Example 39, in methanol (20 ml) p-toluenesulfonic acid (1 g) is added. The solution is allowed to stay at room temperature for 5 hr. then diluted with ether. The organic layer is washed with water, dried (MgSO$_4$) and evaporated to dryness. Chromatographic purification of the residue on 25 g silica gel with ether-hexane (1:4) affords 3-decen-1-yn-5-one.

A solution of the latter compound (1.93 g) in hexane (20 ml) containing quinoline (1 ml) and Lindlar catalyst (100 mg) is hydrogenated at room temperature and atmospheric pressure. After the absorption of 296 ml of hydrogen, the reaction mixture is filtered through diatomaceous earth, washed with 10% hydrochloric acid, then with water, dried and the hexane evaporated to give the title compound, identical to the product of Example 38.

In the same manner but replacing 3-(dimethylamino)-1-decyn-5-one with an equivalent amount of 3-(dimethylamino)-1-heptyn-5-one, 3-(dimethylamino)-1-octyn-5-one, 3-(dimethylamino)-1-nonyn-5-one, 3-(dimethylamino)-1-undecyn-5-one, or 3-(dimethylamino)-1-dodecyn-5-one, then 1,3-heptadien-5-one, 1,3-octadien-5-one, 1,3-nonadien-5-one, 1,3-undecadien-5-one and 1,3-dodecadien-5-one are obtained, respectively.

EXAMPLE 41

Diethyl trans-2-(3-Oxo-1-octenyl)cyclopropane-1,1-dicarboxylate[VI, $R^2 = H$, $R^4 = C_2H_5$ and $(c) = (CH_2)_4$]

To a solution of diethylbromomalonate (2.87 g) in absolute ethanol (3 ml) is added simultaneously sodium ethoxide (from 276 mg sodium) in ethanol (6 ml) and 1,3-decadien-5-one (1.9 g), described in Example 40, in ethanol (3 ml). The sodium ethoxide is added over a period of 20 min. and the dienone over a period of 10 minutes. The mixture is stirred at 0° C. for 3 hr., then at room temperature for 16 hr., acidified with 0.5 ml of acetic acid and the sodium bromide is separated by filtration and washed with benzene. Evaporation of the solvent affords the amide product, which is subject to chromatography on 350 g silica gel elution with ether-hexane (1:4) to give the title compound, nmr (CDCl$_3$) δ 0.88 (t, 3H), 4.18 (q, 4H), 6.22 (s, 1H), 6.28 (s, 1H).

In the same manner but replacing 1,3-decadien-5-one with an equivalent amount of 1,3-heptadien-5-one, 1,3-octadien-5-one, 1,3-nonadien-5-one, 1,3-undecadien-5-one or 1,3-dodecadien-5-one, then diethyl trans-2-(3-oxo-1-pentenyl)cyclopropane-1,1-dicarboxylate, diethyl trans-2-(3-oxo-1-hexenyl)cyclopropane-1,1-dicarboxylate, diethyl trans-2-(3-oxo-1-heptenyl)-cyclopropane-1,1-dicarboxylate, diethyl trans-2-(3-oxo-1-nonenyl)-cyclopropane-1,1-dicarboxylate, and diethyl trans-2-(3-oxo-1-decenyl)-cyclopropane-1,1-dicarboxylate are obtained respectively.

Likewise the corresponding dimethyl and dipropyl esters of the above compounds of formula VI are obtained when diethylbromomalonate is replaced by dimethyl or dipropyl bromomalonate, respectively, in the procedure of this example.

EXAMPLE 42

Dimethyl trans-2-(3-Hydroxy-1-octenyl)cyclopropane-1,1-dicarboxylate [II, $R^2 = H$, $R^4 = CH_3$, $R^5 = H$ and $(c) = (CH_2)_4$]

A solution of 5.5 g of sodium borohydride in 50 ml. of 95% ethanol is added to a solution of the compound of formula VI, dimethyl trans-2-(3-oxo-1-octenyl)cyclopropane-1,1-dicarboxylate (35 g), described in Example 2. After 15 min. at room temperature the mixture is cooled in ice and rendered neutral by the addition of acetic acid. Water is added and the mixture extracted with ethyl-acetate. The extract was dried (Na$_2$SO$_4$) and the evaporated. The residue is purified by chromatography on silica gel to afford the title compound, nmr (CDCl$_3$) δ 0.90 (t, 3H), 2.33 (1H), 3.73 (s, 3H) 4.05 (m, 1H).

By following the procedure of Example 42 and utilizing the appropriate compound of formula VI then other compounds of formula II ($R^5 = H$) are prepared. Examples of such compounds of formula II are listed in Table II. In each case the compound of formula VI used as starting material is noted by the Example in which it is prepared.

TABLE II

| Ex. | No. of Ex. in which Starting Material is Prepared | Product: (Prefix Listed Below)Cyclo-Propane-1,1-Dicarboxylate |
|---|---|---|
| 43 | 3 | dimethyl trans-2-(3-hydroxy-1-pentenyl) |
| 44 | 4 | diethyl trans-2-(3-hydroxy-1-octenyl) |
| 45 | 5 | dimethyl trans-2-(3-hydroxy-1-heptenyl) |
| 46 | 6 | dimethyl trans-2-(3-hydroxy-1-nonenyl) |
| 47 | 7 | dimethyl trans-2-(3-hydroxy-1-decenyl) |
| 48 | 8 | dimethyl trans-2-(3-hydroxy-1,5-heptadienyl) |
| 49 | 9 | dimethyl trans-2-(3-hydroxy-1,5-octadienyl) |
| 50 | 10 | dimethyl trans-2-(3-hydroxy-1,5-nonadienyl) |
| 51 | 11 | dimethyl trans-1-(3-hydroxy-1,5-decadienyl) |
| 52 | 12 | dimethyl trans-3-methyl-2-(3-hydroxy-1-pentenyl) |
| 53 | 13 | dimethyl-trans-3-methyl-2-(3-hydroxy-1-hexenyl) |
| 54 | 14 | dimethyl-trans-3-methyl-2-(3-hydroxy-1-heptenyl) |
| 55 | 15 | dimethyl-trans-3-methyl-2-(3-hydroxy-1-octenyl) |
| 56 | 16 | dimethyl-trans-3-methyl-2-(3-hydroxy-1-nonenyl) |
| 57 | 17 | dimethyl-trans-3-methyl-2-(3-hydroxy-1-decenyl) |
| 58 | 18 | dimethyl trans-3-methyl-2-(3-hydroxy-1,5-heptadienyl) |
| 59 | 19 | dimethyl trans-3-methyl-2-(3-hydroxy-1,5-octadienyl) |
| 60 | 20 | dimethyl trans-3-methyl-2-(3-hydroxy-1,5-nonadienyl) |
| 61 | 21 | dimethyl trans-3-methyl-2-(3-hydroxy-1,5-decadienyl) |
| 62 | 22 | dimethyl trans-3-ethyl-2-(3-hydroxy-1-pentenyl) |
| 63 | 23 | diethyl trans-3-ethyl-2-(3-hydroxy-1-octenyl) |
| 64 | 24 | dimethyl trans-3-ethyl-2-(3-hydroxy-1-decenyl) |
| 65 | 25 | diethyl trans-3-ethyl-2-(3-hydroxy-1,5-heptadienyl) |
| 66 | 26 | diethyl trans-3-ethyl-2-(3-hydroxy-1,5-octadienyl) |
| 67 | 27 | dimethyl trans-3-propyl-2-(3-hydroxy-1-hexenyl) |
| 68 | 28 | dimethyl trans-3-propyl-2-(3-hydroxy-1-octenyl) |
| 69 | 29 | diethyl trans-3-isopropyl-2-(3-hydroxy-1-nonenyl) |
| 70 | 30 | dimethyl trans-3-isopropyl-2-(3-hydroxy-1,5-nonadienyl) |
| 71 | 31 | dimethyl trans-3-propyl-2-(3-hydroxy-1,5-decadienyl) |
| 72 | 32 | dimethyl trans-3-(acetoxymethyl)-2-(3-hydroxy-1-heptenyl) |
| 73 | 33 | diethyl trans-3-(acetoxymethyl)-2-(3-hydroxy-1-octenyl), $\gamma_{max}^{film}$ 3600, 3500, 1730 cm$^{-1}$ |
| 74 | 34 | diethyl trans-3-(acetoxymethyl)-2-(3-hydroxy-1-decenyl) |
| 75 | 35 | diethyl trans-3-(acetoxymethyl)-2-(3-hydroxy-1,5-heptadienyl) |
| 76 | 36 | diethyl trans-3-(acetoxymethyl)-2-(3-hydroxy-1,5-octadienyl) |

EXAMPLE 77

Dimethyl trans-2-{3-[(Tetrahydropyran-2-yl)oxy]-1-octenyl}cyclopropane-1,1-dicarboxylate [II, $R^2$=H, $R^4$=CH$_3$, $R^5$=tetrahydropyran-2-yl and (c)=(CH$_2$)$_4$]

A solution of dimethyl trans-2-(3-hydroxy-1-octenyl)cyclopropane-1,1-dicarboxylate (22.4 g), described in Example 42, dihydropyran (80 ml, distilled over sodium) and p-toluenesulfonic acid monohydrate (300 mg) is allowed to stand at room temperature for 30 min. After adding a few ml of 10% Na$_2$CO$_3$ solution the mixture is extracted with ether. The ether extract is washed with water, dried (Na$_2$SO$_4$) and evaporated. Purification of the residue by chromatography on silica gel gives the title compound.

In the same manner but using an equivalent amount of one of the compounds of formula II ($R^5$=H), for example, the compounds listed in Examples 43 to 76, instead of dimethyl trans-2-(3-hydroxy-1-octenyl)cyclopropane-1,1-dicarboxylate, then the corresponding tetrahydropyranyl ether compound of formula II ($R^5$=tetrahydropyranyl) is obtained, for example, the corresponding tetrahydropyranyl ether compounds of Examples 43 to 76, respectively. More specifically exemplified, in the same manner diethyl trans-3-(acetoxymethyl)-2-(3-hydroxy-1-octenyl)cyclopropane-1,1-dicarboxylate (Example 73) gives diethyl trans-3-(acetoxymethyl)-2-{3-[(tetrahydropyran-2-yl)oxy]-1-octenyl}-cyclopropane-1,1-dicarboxylate, $\gamma_{max}^{film}$ 1740, 1720 cm$^{-1}$, and dimethyl trans-3-methyl-2-(3-hydroxy-1,5-heptadienyl)cyclopropane-1,1-dicarboxylate (Example 58) gives dimethyl trans-2-{3-[(tetrahydropyran-2-yl)oxy]-1,5-heptadienyl}cyclopropane-1,1-dicarboxylate.

EXAMPLE 78

7-Hydroxy-5-heptynoic Acid (XII, p=3)

By following the procedure of A. I. Rachlin, et al., cited above, 6-chloro-2-hexyn-1-ol is prepared by condensing propargyl alcohol tetrahydropyran-2-yl ether and the dihaloalkane of formula VIII, 1-bromo-3-chloropropane, to give 1-[(tetrahydropyran-2-yl)oxy]-6-chloro-2-hexyne, which is then converted to the desired compound followed by hydrolysis in the presence of sulfuric acid. The 6-chloro-2-hexyn-1-ol (280 g) is dissolved in ethanol (2.8 l) then water (560 ml) and potassium cyanide (290 g) is added and the mixture stirred and refluxed for 20 hr. Potassium hydroxide (768 g) and water (500 ml) are added and the stirred mixture kept at reflux for an additional 20 hr. Methanol is evaporated and the water phase is acidified with concentrated HCl and extracted with ether for 2 days in a continuous liquid-liquid extractor. The ether extract is dried (Na$_2$SO$_4$) and concentrated to give the title compound, nmr (CDCl$_3$) δ 4.22 (m, 2H), 7.41 (broad, 2H).

EXAMPLE 79

Methyl 7-Bromo-5-heptynoate (XV, p=3 and R=CH$_3$)

To a solution of 7-hydroxy-5-heptynoic acid (88.2 g), described in Example 78, in anhydrous ether (300 ml) and pyridine (12 ml) is added dropwise phosphorus tribromide (67.5 g) at 10° C. The solution is stirred at room temperature for 30 min. then cooled to 5° C. and 10% HCl (120 ml) is added slowly. The organic layer is washed with water and 10% sodium carbonate, dried ($Na_2SO_4$) and concentrated. The residue is distilled under reduced pressure to give 7-bromo-5-heptynoic acid, b.p. 146° C., 0.8 mm.

The latter compound is esterifed in the following manner. The latter compound (156 g) is dissolved in absolute methanol (1.5 l). p-Toluenesulfonic acid (78 g) is added to the solution which is then heated at reflux for 2 hr. Thereafter the solvent is evaporated. The residue is dissolved in water and the aqueous solution extracted with benzene. The extract is washed with 10% $Na_2CO_3$ and then water until neutral, dried ($Na_2SO_4$) and concentrated. The residue is distilled to give the title compound, b.p. 70°–80° C. 0.2 mm.

The corresponding ethyl or other lower alkyl esters of the latter compound are likewise prepared according to the preceding esterification procedure by replacing methanol with ethanol or an appropriate corresponding lower alkanol, respectively.

Alternatively, the procedure of this example may be reversed whereby 7-hydroxy-5-heptynoic acid is first subjected to the esterification procedure with methanol and p-toluenesulfonic acid, followed by treatment of the resulting hydroxy ester XIV (p=3 and R=$CH_3$) with phosphorus tribromide as described herein.

By following serially the procedures of Examples 78 and 79 but using the dihaloalkanes of formula VIII, 1-bromo-2-chloroethane or 1-bromo-4-chlorobutane, instead of 1-bromo-4-chloropropane, then methyl 6-bromo-4-hexynoate and methyl 8-bromo-6-octaynoiate are obtained, respectively.

Furthermore, an equivalent amount of the corresponding α-iodo-ω-chloroalkane used in place of the dihaloalkane of formula VII in the serial application of the procedures of Examples 78 and 79 gives the corresponding chloroester of the bromoester of formula XV; namely, 1-chloro-2-iodoethane, 1-chloro-3-iodopropane and 1-chloro-4-iodobutane yield methyl 6-chloro-4-hexynoate, methyl 7-chloro-5-heptynoate and methyl 8-chloro-6-octynoate, respectively. These latter methyl esters may be used in the manner described below for utilizing the bromoesters of formula XV.

EXAMPLE 80

Trimethyl 3-Heptyne-1,1,7-tricarboxylate (III; (a)=C≡C, p=3, R=$CH_3$ and $R^6$=$CH_3$)

Dimethyl malonate (39.6 g, 0.3 mole) is added slowly with cooling and stirring to a solution of 6.9 g (0.3 atom) of sodium dissolved in 100 ml of absolute methanol and the mixture stirred for 15 min. The bromoester of formula XV, methyl 7-bromo-5-heptynoate (65.7 g, 0.3 mole), described in Example 79, is added dropwise. The mixture is heated at reflux for 1 hr., cooled and diluted with water. The mixture is extracted with ether. The ether extracts are dried ($Na_2SO_4$) and concentrated. The residue is distilled under reduced pressure, to give the title compound, b.p. 153° C./0.4 mm., nmr ($CDCl_3$) δ 3.69, 3.78.

In the same manner but replacing methyl 7-bromo-5-heptynoate with an equivalent amount of methyl 6-bromo-4-hexynoate or methyl 8-bromo-6-octynoate, trimethyl 3-hexyne-1,1,6-tricarboxylate and trimethyl 3-octyne-1,1,8-tricarboxylate are obtained, respectively.

In the same manner but replacing methyl 7-bromo-5-heptynoate with an equivalent amount of methyl 6-bromo-4-hexenoate, methyl 7-bromo-5-heptenoate, methyl 8-bromo-6-octenoate, methyl 6-bromohexenoate, methyl 7-bromoheptanoate, or methyl 8-bromooctanoate, trimethyl 3-hexene-1,1,6-tricarboxylate, trimethyl 3-heptene-1,1,7-tricarboxylate, trimethyl 3-octene-1,1,8-tricarboxylate, trimethyl hexane-1,1,6-tricarboxylate, trimethyl heptane-1,1,7-tricarboxylate and trimethyl octane-1,1,8-tricarboxylate are obtained, respectively.

By using the corresponding ethyl or other lower alkyl ester analogs of the methyl ester starting materials noted above, the corresponding ethyl or other lower alkyl esters of the methyl ester products, noted above, are obtained.

EXAMPLE 81

Trimethyl cis-3-Heptene-1,1,7-tricarboxylate (III, (a)=CH=CH, p=3, R=$CH_3$ and $R^6$=$CH_3$)

Trimethyl 3-heptyne-1,1,7-tricarboxylate (30.5 g), described in Example 80, is hydrogenated in the presence of 1.0 g of Lindlar catalyst [Org. Syn., 46, 89 (1966)] in a solution of 100 ml of ethyl acetate and 1000 ml of hexane. After 4 hr. and absorption of 740 ml of hydrogenation another 1.0 g of catalyst is added. After a further 8 hr. an additional 880 ml of hydrogen is absorbed. No further absorption of hydrogen is observed. After filtering the filtrate is concentrated. The residue is distilled under reduced pressure. The title compound has b.p. 140°–150° C./0.7 mm., nmr ($CDCl_3$) δ 3.55 (1H), 5.41 (m, 2H), identical to the same compound described in Example 80.

In the same manner but using trimethyl 3-hexyne-1,1,6-tricarboxylate or trimethyl 3-octyne-1,1,8-tricarboxylate, trimethyl 3-hexene-1,1,6-tricarboxylate and trimethyl 3-octene-1,1,8-tricarboxylate, identical to the same compounds described in Example 80, are obtained.

EXAMPLE 82

Dimethyl cis, trans-3-(6-Carbomethoxy-2-hexenyl)-4-(3-hydroxy-1-octenyl)-2-oxo-1,3-cyclopentanedicarboxylate (IVa; (a)=CH=CH, p=3, (c)=$(CH_2)_4$, R, $R^4$ and $R^6$=$CH_3$ and $R^5$ and $R^7$=H)

Procedure A [using compound II ($R^5$=tetrahydropyran-2-yl)]

To a mixture of the compound of formula II, dimethyl trans-2-{3-[(tetrahydropyran-2-yl)oxy]-1-octenyl}cyclopropane-1,1-dicarboxylate (20.4 g), described in Example 77, and the compound of formula III, trimethyl cis-3-heptene-1,1,7-tricarboxylate (15.08 g), described in Example 81, a solution of 1.27 g of sodium in 50 ml of methanol is added at room temperature. The methanol is removed under slightly reduced pressure. The residue is heated at 135°–140° C. for 1 hr. while keeping a slightly reduced pressure in the reaction flask. Saturated NaCl solution is added and the mixture rendered neutral with acetic acid. The mixture is extracted with ether. The extract is dried ($Na_2SO_4$) and concentrated. Chromatography of the residue on silica gel yields dimethyl cis, trans-3-(6-carbomethoxy-2-hexenyl)-4-{3-[tetrahydropyran-2-yl)oxy]-1-octenyl}-2-oxo-1,3-cyclopentanedicarboxylate, nmr ($CDCl_3$) δ 0.90 (t, J=6, 3H), 3.68–3.78 (3H), 3.20 (2H), 4.20 (1H).

A solution of the latter compound (10.5 g) in 80 ml of methanol-water (9:1) and 1.0 g of p-toluenesulfonic acid monohydrate is left at room temperature for 15 min. and then rendered neutral with aqueous $NaHCO_3$. The methanol is evaporated and after addition of saturated NaCl, the mixture is extracted with ether. The ether layer is dried (Na$_2$SO$_4$). Evaporation of the solvent gives a residue, which on purification by chromatography on silica gel affords the title compound, nmr (CDCl$_3$) 0.90 (t, J=5, 3H), 3.68, 3.74 and 3.78 (3H), 4.15 (1H), 5.1–5.8 (m, 1H).

Procedure B [using compound II (R$^5$=H)]:

Sodium methoxide [from 0.5 g (0.022 atom) of sodium and 30 ml of absolute methanol] is added at room temperature to a mixture of 5.6 g (0.02 mole) of the compound of formula II, dimethyl trans-2-(3-hydroxy-1-octenyl)cyclopropane-1,1-dicarboxylate, described in Example 42, and 5.4 g (0.02 mole) of the compound of formula III, trimethyl cis-3-heptene-1,1,7-tricarboxylate, described in Example 81, in 10 ml of absolute methanol. After refluxing for 2 hr. the methanol is removed at reduced pressure and the residue adjusted to pH 6 with acetic acid. The mixture is extracted with ether. The ether extract is worked up in the same manner as described for the ether extract in procedure A of this example. In this manner the title compound is obtained, identical to the product of procedure A.

By following the procedures A or B of Example 82 and using the appropriate compounds of formulae II and III as starting materials, other cyclopentanonetriesters of formulae IVa or IVb are prepared. Examples of such compounds of formula IV are listed in Tables III and IIIa together with the requisite starting materials. It is to be noted that when procedure A is used the requisite starting material of formula II is the corresponding tetrahydropyran-2-yl ether derivative of the compound of formula II noted therein; the tetrahydropyran-2-yl ether being prepared by following the procedure described in Example 77. Preparation of the starting materials of formula III, i.e. triesters of formula III, is described in Examples 80 and 81.

TABLE III

| Ex. | NO. OF EXAMPLE IN WHICH STARTING MATERIAL OF FORMULA II IS DESCRIBED | STARTING MATERIAL OF FORMULA III | | | PRODUCT: (PREFIX LISTED BELOW)-2-OXO-1,3-CYCLOPENTANEDI-CARBOXYLATE |
|---|---|---|---|---|---|
| | | (a) | P | R and R$^6$ | |
| 83 | 43 | C≡C | 2 | CH$_3$ | dimethyl trans-3-(5-carbomethoxy-2-pentynyl)-4-(3-hydroxy-1-pentenyl) |
| 84 | 44 | C≡C | 3 | C$_2$H$_5$ | diethyl trans-3-(6-carboethoxy-2-hexynyl)-4-(3-hydroxy-1-octenyl), $\gamma_{max}^{film}$ 3450, 1737, 1225 cm$^{-1}$. |
| 85 | 45 | C≡C | 4 | CH$_3$ | dimethyl trans-3-(7-carbomethoxy-2-heptynyl)-4-(3-hydroxy-1-heptenyl) |
| 86 | 46 | CH=CH | 2 | CH$_3$ | dimethyl cis, trans-3-(5-carbomethoxy-2-pentenyl)-4-(3-hydroxy-1-nonenyl) |
| 87 | 47 | CH=CH | 3 | CH$_3$ | dimethyl cis, trans-3-(6-carbomethoxy-2-hexenyl)-4-(3-hydroxy-1-decenyl) |
| 88 | 48 | CH=CH | 4 | CH$_3$ | dimethyl cis, trans-3-(7-carbomethoxy-2-heptenyl)-4-(3-hydroxy-1,5-heptadienyl) |
| 89 | 49 | CH$_2$CH$_2$ | 2 | CH$_3$ | dimethyl trans-3-(5-carbomethoxypentyl)-4-(3-hydroxy-1,5-octadienyl) |
| 90 | 50 | CH$_2$CH$_2$ | 3 | CH$_3$ | dimethyl trans-3-(6-carbomethoxyhexyl)-4-(3-hydroxy-1,5-nonadienyl) |
| 91 | 51 | CH$_2$CH$_2$ | 4 | CH$_3$ | dimethyl trans-3-(7-carbomethoxyheptyl)-4-(3-hydroxy-1,5-decadienyl) |
| 92 | 52 | C≡C | 2 | CH$_3$ | dimethyl trans-3-(5-carbomethoxy-2-pentynyl)-4-(3-hydroxy-1-pentenyl)-5-methyl |
| 93 | 53 | C≡C | 3 | CH$_3$ | dimethyl trans-3-(6-carbomethoxy-2-hexynyl)-4-(3-hydroxy-1-hexenyl)-5-methyl |
| 94 | 54 | C≡C | 4 | CH$_3$ | dimethyl trans-3-(7-carbomethoxy-2-heptynyl)-4-(3-hydroxy-1-heptenyl)-5-methyl |
| 95 | 55 | CH=CH | 2 | CH$_3$ | dimethyl cis, trans-3-(5-carbomethoxy-2-pentenyl)-4-(3-hydroxy-1-octenyl)-5-methyl |
| 96 | 56 | CH=CH | 3 | CH$_3$ | dimethyl cis, trans-3-(6-carbomethoxy-2-hexenyl)-4-(3-hydroxy-1-nonenyl)-5-methyl |
| 97 | 57 | CH=CH | 4 | CH$_3$ | dimethyl cis, trans-3-(7-carbomethoxy-2-heptenyl)-4-(3-hydroxy-1-decenyl)-5-methyl |
| 98 | 58 | CH$_2$CH$_2$ | 2 | CH$_3$ | dimethyl trans, cis-3-(5-carbomethoxypentyl)-4-(3-hydroxy-1,5-heptadienyl)-5-methyl |
| 99 | 59 | CH$_2$CH$_2$ | 3 | CH$_3$ | dimethyl trans, cis-3-(6-carbomethoxyhexyl)-4-(3-hydroxy-1,5-octadienyl)-5-methyl |
| 100 | 60 | CH$_2$CH$_2$ | 4 | CH$_3$ | dimethyl trans, cis-3-(7-carbomethoxyheptyl)-4-(3-hydroxy-1,5-nonadienyl)-5-methyl |
| 101 | 61 | C≡C | 2 | CH$_3$ | dimethyl trans, cis-3-(5-carbo- |

TABLE III-continued

| Ex. | NO. OF EXAMPLE IN WHICH STARTING MATERIAL OF FORMULA II IS DESCRIBED | STARTING MATERIAL OF FORMULA III (a) | P | R and $R^6$ | PRODUCT: (PREFIX LISTED BELOW)-2-OXO-1,3-CYCLOPENTANEDI-CARBOXYLATE |
|---|---|---|---|---|---|
| | | | | | methoxy-2-pentynyl)-4-(3-hydroxy-1,5-decadienyl)-5-methyl |
| 102 | 62 | C≡C | 3 | $CH_3$ | dimethyl trans, cis-3-(6-carbomethoxy-2-hexynyl)-4-(3-hydroxy-1-pentenyl)-5-ethyl |
| 103 | 63 | C≡C | 4 | $C_2H_5$ | diethyl trans-3-(7-carbethoxy-2-heptynyl)-4-(3-hydroxy-1-octenyl)-5-ethyl |
| 104 | 64 | CH=CH | 2 | $CH_3$ | dimethyl cis, trans-3-(5-carbomethoxy-2-pentenyl)-4-(3-hydroxy-1-decenyl)-5-ethyl |
| 105 | 65 | CH=CH | 3 | $C_2H_5$ | diethyl cis, trans, cis-3-(6-carboethoxy-2-hexenyl)-4-(3-hydroxy-1,5-heptadienyl)-5-ethyl |
| 106 | 66 | CH=CH | 4 | $C_2H_5$ | diethyl cis, trans, cis-3-(7-carboethoxy-2-heptenyl)-4-(3-hydroxy-1,5-octadienyl)-5-ethyl |
| 107 | 67 | $CH_2CH_2$ | 2 | $CH_3$ | dimethyl trans-3-(5-carbomethoxypentyl)-4-(3-hydroxy-1-hexenyl)-5-propyl |
| 108 | 68 | $CH_2CH_2$ | 3 | $CH_3$ | dimethyl trans-3-(6-carbomethoxyhexyl)-4-(3-hydroxy-1-octenyl)-5-propyl |
| 109 | 69 | $CH_2CH_2$ | 4 | $C_2H_5$ | diethyl trans-3-(7-carboethoxyheptyl)-4-(3-hydroxy-1-nonenyl)-5-isopropyl |
| 110 | 70 | C≡C | 2 | $CH_3$ | dimethyl trans, cis-3-(5-carbomethoxy-2-pentynyl)-4-(3-hydroxy-1,5-nonadienyl)-5-isopropyl |
| 111 | 71 | C≡C | 3 | $CH_3$ | dimethyl trans, cis-3-(6-carbomethoxy-2-hexynyl)-4-(3-hydroxy-1,5-decadienyl)-5-propyl |

Table IIIa

| EX. | NO. OF EXAMPLE IN WHICH STARTING MATERIAL OF FORMULA II IS DESCRIBED | STARTING MATERIAL OF FORMULA III (a) | p | R and $R^6$ | PRODUCT: (PREFIX LISTED BELOW)-5-(HYDROXYMETHYL)-2-OXO-1-CYCLO-PENTANECARBOXYLIC ACID γ-LACTONE |
|---|---|---|---|---|---|
| 112 | 72 | C≡C | 4 | $CH_3$ | trans-3-carbomethoxy-3-(7-carbomethoxy-2-heptynyl)-4-(3-hydroxy-1-heptenyl) |
| 113 | 73 | $CH_2CH_2$ | 3 | $C_2H_5$ | trans-3-carboethoxy-3-(6-carboethoxyhexyl)-4-(3-hydroxy-1-octenyl), $\gamma_{max}^{film}$ 3500, 1770, 1730 cm$^{-1}$. |
| 114 | 74 | CH=CH | 3 | $C_2H_5$ | cis, trans-3-carboethoxy-3-(6-carboethoxy-2-hexenyl)-4-(3-hydroxy-1-decenyl) |
| 115 | 75 | $CH_2CH_2$ | 3 | $C_2H_5$ | trans, cis-3-carboethoxy-3-(6-carboethoxyhexyl)-4-(3-hydroxy-1,5-heptadienyl) |
| 116 | 76 | $CH_2CH_2$ | 4 | $C_2H_5$ | trans, cis-3-carboethoxy-3-(7-carboethoxyheptyl)-4-(3-hydroxy-1,5-octadienyl) |

EXAMPLE 117 trans, cis-7-[2-(3-Hydroxy-1-octenyl)-5-oxocyclopentyl]-5-heptenoic Acid (I; (a)=CH=CH, p=3, (b)=CH=CH, (c)=$(CH_2)_4$ and R, $R^1$ and $R^2$=H)

The cyclopentanonetriester of formula IV, dimethyl cis,trans-3-(6-carbomethoxy-2-hexenyl)-4-(3-hydroxy-1-octenyl)-2-oxo-1,3-cyclopentanedicarboxylate (11.2 g), described in Example 82, is heated to reflux for 1 hr. in a solution of sodium hydroxide (13.4 g) in 80 ml of water and 110 ml of methanol. The mixture is cooled, adjusted to pH 5 with 2 N HCl, diluted with saturated sodium chloride solution and extracted with ether. The ether extract is dried ($Na_2SO_4$) and concentrated to yield the title compound as a mixture of $C_{15}$ epimers is separated by silica gel chromatography using hexane: chloroform: acetic acid: 10:20:1. The less polar epimer is designated epimer A, nmr ($CDCl_3$) δ 1.05 (t, J=5, 3H), 4.20 (1H), 5.33–5.78 (1H), 6.38 (2H). The more polar epimer is designated epimer B, nmr ($CDCl_3$) δ 1.05 (t, J=5, 3H) 4.18 (1H), 5.30–5.77 (1H), 6.74 (2H).

By following the procedure of Example 117 and using the appropriate cyclopentanonetriester of formula IV, for example those described in Examples 83 to 116, then other compounds of formula I in which R and R¹ are hydrogen are obtained. Examples of such compounds of formula I are listed in Table IV together with the requisite cyclopentanonetriester starting material, the latter compound being noted by the example describing its preparation.

TABLE IV

| EXAMPLE | No. of Example in which cyclo-pentanonetriester of formula IV is prepared | PRODUCT: |
|---|---|---|
| 118 | 83 | trans-6-[2-(3-hydroxy-1-pentenyl)-5-oxocyclopentyl]-4-hexynoic acid |
| 119 | 84 | trans-7-[2-(3-hydroxy-1-octenyl)-5-oxocyclopentyl]-5-heptynoic acid, $\gamma_{max}^{film}$ 3475 and 1735 cm$^{-1}$ |
| 120 | 85 | trans-8-[2-(3-hydroxy-1-heptenyl)-5-oxocyclopentyl]-6-octynoic acid |
| 121 | 86 | trans,cis-6-[2-(3-hydroxy-1-nonenyl)-5-oxocyclopentyl]-4-hexenoic acid |
| 122 | 87 | trans,cis-7-[2-(3-hydroxy-1-decenyl)-5-oxocyclopentyl]-5-heptenoic acid |
| 123 | 88 | trans,cis,cis-8-[2-(3-hydroxy-1,5-heptadienyl)-5-oxoycylopentyl]-6-octenoic acid |
| 124 | 89 | trans,cis,cis-6-[2-(3-hydroxy-1,5-octadienyl)-5-oxocyclopentyl]hexanoic acid |
| 125 | 90 | trans,cis,cis-7-[2-(3-hydroxy-1,5-nonadienyl)-5-oxocyclopentyl]heptanoic acid |
| 126 | 91 | trans,cis,cis-8-[2-(3-hydroxy-1,5-decadienyl)-5-oxocyclopentyl]octanoic acid |
| 127 | 92 | trans-6-[2-(3-hydroxy-1-pentenyl)-3-methyl-5-oxocyclopentyl]-4-hexynoic acid |
| 128 | 93 | trans-7-[2-(3-hydroxy-1-hexenyl)-3-methyl-5-oxocyclopentyl]-5-heptynoic acid |
| 129 | 94 | tran-8-[2-(3-hydroxy-1-heptenyl)-3-methyl-5-oxocyclopentyl]-6-octynoic acid |
| 130 | 95 | trans,cis-6-[2-(3-hydroxy-1-octenyl)-3-methyl-5-oxocyclopentyl]-4-hexenoic acid |
| 131 | 96 | trans,cis-7-[2-(3-hydroxy-1-nonenyl)-3-methyl-5-oxocyclopentyl]-5-heptenoic acid |
| 132 | 97 | trans,cis-8-[2-(3-hydroxy-1-decenyl)-3-methyl-5-oxocyclopentyl]-6-octenoic acid |
| 133 | 98 | trans,cis-6-[2-(3-hydroxy-1,5-heptadienyl)-3-methyl-5-oxocylopentyl]hexanoic acid |
| 134 | 99 | trans,cis-7-[2-(3-hydroxy-1,5-octadienyl)-3-methyl-5-oxocyclopentyl]heptanoic acid |
| 135 | 100 | trans,cis-8-[2-(3-hydroxy-1,5-nonadienyl)-3-methyl-5-oxocyclopentyl]octanoic acid |
| 136 | 101 | trans,cis-6-[2-(3-hydroxy-1,5-decadienyl)-3-methyl-5-oxocyclopentyl]-4-hexynoic acid |
| 137 | 102 | trans-7-[2-(3-hydroxy-1-pentenyl)-3-ethyl-5-oxocyclopentyl]5-heptynoic acid |
| 138 | 103 | trans-8-[2-(3-hydroxy-1-octenyl)-3-ethyl-5-oxocyclopentyl]-6-octynoic acid |
| 139 | 104 | trans,cis-6-[2-(3-hydroxy-1-decenyl)-3-ethyl-5-oxocyclopentyl]-4-hexenoic acid |
| 140 | 105 | trans,cis,cis-7-[2-(3-hydroxy-1,5-heptadienyl)-3-ethyl-5-oxocyclopentyl]-5-heptenoic acid |
| 141 | 106 | trans,cis,cis-8-[2-(3-hydroxy-1,5-octadienyl)-3-ethyl-5-oxocyclopentyl]-6-octenoic acid |
| 142 | 107 | trans-6-[2-(3-hydroxy-1-hexenyl)-3-propyl-5-oxocyclopentyl]hexanoic acid |
| 143 | 108 | trans-7-[2-(3-hydroxy-1-octenyl)-3-propyl-5-oxocyclopentyl]heptanoic acid |
| 144 | 109 | trans-8-[2-(3-hydroxy-1-nonenyl)-3-isopropyl-5-oxocyclopentyl]octanoic acid |
| 145 | 110 | trans,cis-6-[2-(3-hydroxy-1,5-nonadienyl)-3-isopropyl-5-oxocyclopentyl]-4-hexynoic acid |
| 146 | 111 | trans,cis-7-[2-(3-hydroxy-1,5-decadienyl)-3-propyl-5-oxocyclopentyl]-5-heptynoic acid |
| 147 | 112 | trans-8-[2-(3-hydroxy-1-heptenyl)-3-(hydroxymethyl)-5-oxocyclopentyl-6-octynoic acid |
| 148 | 113 | trans-7-[2-(3-hydroxy-1-octenyl)-3-(hydroxymethyl)-5-oxocyclopentyl]heptanoic acid, $\gamma_{max}^{film}$ 3400–3600, 1710 cm$^{-1}$ |
| 149 | 114 | trans,cis-7-[2-(3-hydroxy-1-decenyl)-3-(hydroxymethyl)-5-oxocyclopentyl]-5-heptanoic acid |
| 150 | 115 | trans,cis-7-[2-(3-hydroxy-1,5-heptadienyl)-3-(hydroxymethyl)-5-oxocyclopentyl]heptanoic acid |
| 151 | 116 | trans,cis-8-[2-(3-hydroxy-1,5-octadienyl)-3-(hydroxymethyl)-5-oxocyclopentyl]octanoic acid |

EXAMPLE 152

Methyl trans, cis-7-[2-(3-hydroxy-1-octenyl)-5-oxocyclopentyl]-5-heptenoate (I; (a)=CH=CH, p=3, (b)=CH=CH, (c)=(CH₂)₄, R=CH₃ and R¹ and R²=H)

The compound of formula I, trans,cis-7-[2-(3-hydroxy-1-octenyl)-5-oxocyclopentyl]-5-heptenoic acid (16.0 g), described in Example 117, is dissolved in 150 ml of absolute methanol. Perchloric acid (5 to 10 drops) is added to the solution which is kept at room temperature for 2 hr. Thereafter the mixture is concentrated. The residue is diluted with water and shaken with ether. The ether layer is washed with 10% $Na_2CO_3$ and then water until neutral, dried ($MgSO_4$) and concentrated to yield the title compound, $\gamma_{max}^{CHCl_3}$ 1705 cm$^{-1}$.

In the same manner but using the appropriate choice of the compound of formula I and lower alkanol, then other corresponding esters of formula I (R=lower alkyl) are prepared. For example, the choice of trans-8-[2-(3-hydroxy-1-heptenyl)-5-oxocyclopentyl]-6-octynoic acid (Example 120) and ethanol, instead of the compound of formula I and methanol in the procedure of this example gives ethyl trans-8-[2-(3-hydroxy-1-heptenyl)-5-oxocyclopentyl]-6-octynoate. Similarly the choice of trans-7-[2-(3-hydroxy-1-octenyl)-3-(hydroxymethyl)-5-oxocyclopentyl]heptanoic acid (Example 148) and methanol gives methyl trans-7-[2-(3-hydroxy-1-octenyl)-3-(hydroxymethyl)-5-oxocyclopentyl]heptanoate, $\gamma_{max}^{film}$ 3420, 1730 cm$^{-1}$.

EXAMPLE 153

Methyl trans,cis-7-[2-(3-acetoxy-1-octenyl)-5-oxocyclopentyl]-5-heptenoate

A solution of the compound of formula I, methyl trans,cis-7-[2-(3-hydroxy-1-octenyl)-5-oxocyclopentyl]-5-heptenoate (5 g), described in Example 161, in 50 ml of pyridine and 50 ml of acetic anhydride is stirred at room temperature for 4 hr. The solution is diluted with ice-water and extracted with ether. The ether is washed with 10% $H_2SO_4$, water 10% $Na_2CO_3$ and water, dried ($Na_2SO_4$) and evaporated to give the title compound.

In the same manner but using the appropriate choice of compound of formula I (R¹=H) and lower alkanoic anhydride, then other compounds of formula I (R=lower alkanoyl and if R² is CH₂OR³ then R³ is lower alkanoyl) are prepared. For example the choice of trans-8-[2-(3-hydroxy-1-nonenyl)-3-isopropyl-5-oxocyclopentyl]octanoic acid (Example 144) and propionic anhydride instead of the compound of formula I and acetic anhydride noted in the procedure of this Example, give trans-8-[2-(3-propionoxy-1-nonenyl)-3-isopropyl-5-oxocyclopentyl]octanoic acid. Similarly, ethyl trans-8-[2-(3-hydroxy-1-heptenyl)-5-oxocyclopentyl]-6-octynoate (see Example 161) and butyric anhydride gives ethyl trans-8-[2-(3-butyryloxy-1-heptenyl)-5-oxocyclopentyl]-6-octynate.

We claim:

1. A compound of the formula

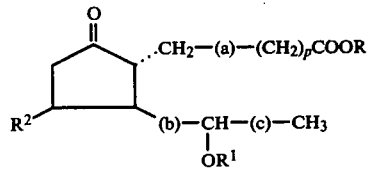

in which (a) is CH₂CH₂, p is an integer from 2 to 4, (b) is trans CH=CH, (c) is (CH₂)$_q$ wherein q is an integer from 1 to 6, R is hydrogen or lower alkyl, R¹ is hydrogen and R² is CH₂OH.

2. trans-7-[2-(3-Hydroxy-1-octenyl)-3-(hydroxymethyl)-5-oxocyclopentyl]heptanoic acid.

3. Methyl trans-7-[2-(3-hydroxy-1-octenyl)-3-(hydroxymethyl)-5-oxocyclopentyl]heptanoate.

* * * * *